(12) United States Patent
Taeusch

(10) Patent No.: US 6,180,142 B1
(45) Date of Patent: Jan. 30, 2001

(54) REDUCTION OF SURFACTANT INACTIVATION IN PULMONARY SURFACTANT THERAPY

(75) Inventor: H. William Taeusch, San Francisco, CA (US)

(73) Assignee: The Regents of the University of California, Oakland, CA (US)

(*) Notice: Under 35 U.S.C. 154(b), the term of this patent shall be extended for 0 days.

(21) Appl. No.: 09/138,435

(22) Filed: Aug. 21, 1998

(51) Int. Cl.[7] .......................... A61K 35/42; A01N 57/26
(52) U.S. Cl. .............................. 424/557; 514/78
(58) Field of Search .................. 514/78; 424/557

(56) References Cited

U.S. PATENT DOCUMENTS

| | | | | |
|---|---|---|---|---|
| 4,312,860 | * | 1/1982 | Clements | 424/195 |
| 4,826,821 | * | 5/1989 | Clements | 514/78 |
| 5,108,759 | * | 4/1992 | Ranney | 424/493 |
| 5,110,806 | * | 5/1992 | Clements | 514/78 |
| 5,855,913 | * | 1/1999 | Hanes et al. | 424/489 |
| 5,885,974 | * | 3/1999 | Danielov | 514/109 |

FOREIGN PATENT DOCUMENTS

| | | |
|---|---|---|
| WO 96/19197 | 6/1996 | (WO). |
| WO 97/35882 | 10/1997 | (WO). |
| WO 99/09955 | 3/1999 | (WO). |

OTHER PUBLICATIONS

Galan et al. Obstetrics and Genecology, Oct. 1992, vol. 80, No. 4, pp. 604–608.*
Van Oss et al. Separation Science and Technology, 1987, 22(6), pp. 1515–1526.*
H.W. Taeusch, *Surfactant Therapy for Lung Disease* (1995) Marcel Dekker, Inc., New York.*

* cited by examiner

Primary Examiner—Sandra E. Saucier
Assistant Examiner—Vera Afremova
(74) Attorney, Agent, or Firm—Townsend and Townsend and Crew LLP

(57) ABSTRACT

Nonionic hydrophilic polymers or carbohydrates are administered either individually or in conjunction with therapeutically active pulmonary surfactants for the treatment of a variety of lung ailments. Included among the activities of these agents is their ability to reduce the inactivation of the surfactants by endogenous substances present in the lung.

30 Claims, 1 Drawing Sheet

REDUCTION OF SURFACTANT INACTIVATION IN PULMONARY SURFACTANT THERAPY

BACKGROUND OF THE INVENTION

1. Field of the Invention

This invention resides in the fields of respiratory distress syndrome, pre-natal and neonatal infant care in general, and lung diseases of both infants and adults. In particular, this invention addresses issues related to the use of naturally-occurring surfactants, modifications of natural surfactants, and synthetic analogs of natural surfactants as therapeutic agents for the treatment of various conditions.

2. Description of the Prior Art

Acute lung injury is a major clinical problem that includes diseases as disparate as acute respiratory distress syndrome in adults, neonatal respiratory distress syndrome, meconium aspiration pneumonia in newborn infants, bacterial and viral pneumonia, pneumonia caused by aspiration of stomach contents, smoke inhalation, and near drowning. Respiratory distress syndrome, for example, is a common disorder in premature infants, and interest in this disorder among pediatricians and pathologists has grown since the 1940s. Within the last twenty years, however, the use of exogenous pulmonary surfactants has emerged as an effective therapy for the treatment and prevention of this disorder. The use of pulmonary surfactants was first reported by Fujiwara and coworkers in 1980 whose studies showed the successful reduction of respiratory distress in preterm infants by the instillation of bovine lung surfactant into the trachea of the infants. Subsequent work by Fujiwara and others has led to the use of a variety of mammalian-derived lung surfactants as therapeutic agents, particularly surfactants that have been extracted, supplemented or otherwise treated to improve their effectiveness. With these advances in surfactant therapy, neonatal deaths and various related lung diseases no longer have the high morbidity rates that they once had.

Unfortunately, a significant percentage of cases fail to respond adequately to surfactant therapy, experiencing instead only a transitory or minimal response. Numerous explanations for this have been offered, each citing the inactivation of surfactant in situ by one or more substances that are normally absent from the alveolar spaces. Aside from the inactivation of exogenous surfactants, endogenous surfactants can be inactivated as well, and this has been implicated as the cause or one of the contributing factors or symptoms of several of the various disease conditions listed in the preceding paragraph. In either case, the substances suspected of causing inactivation include blood, plasma proteins, serum proteins, lipids, and meconium, which is the mass of mucous, desquamated epithelial cells, lanugo, and vernix caseosa that collects in the fetal intestine.

In some cases, inactivation of surfactant, whether exogenous or endogenous, has been reduced by increasing the amount of surfactant relative to the inactivating substance. Inactivation has also been reduced by the administration or co-administration of the surfactant-associated proteins SP-A, SP-B, and SP-C. These proteins are not readily available, however, since they must either be extracted from naturally-occurring surfactants or synthesized by protein synthesis techniques. Accordingly, the search for substances that are effective in countering the various forms of inactivation continues.

SUMMARY OF THE INVENTION

It has now been discovered that one can reduce or eliminate the inactivation of exogenous therapeutic pulmonary surfactants by administering nonionic hydrophilic polymers or carbohydrates in conjunction with the surfactants. Thus, a composition containing as active ingredients (a) a surfactant that is effective in the abatement of pulmonary disorders and (b) either a biocompatible nonionic hydrophilic polymer or a biocompatible carbohydrate is discovered to be an effective therapeutic agent for the treatment of such disorders, in many cases to a degree that is unexpectedly greater than that achieved with administration of the surfactant alone. The invention thus extends to such combinations as novel compositions of matter as well as to the administration of such combinations as novel means of treating, reducing or preventing of such disorders.

An extension of this discovery is the usefulness of the nonionic hydrophilic polymers and carbohydrates, either by themselves or in combination with exogenous pulmonary surfactants to remove thick secretions from the airway in respiratory conditions such as cystic fibrosis, asthma, bronchiectasis, and bacterial pneumonia, and for patients who are at risk of tube blockage while being maintained on assisted ventilation.

A further extension of this discovery is the usefulness of the nonionic hydrophilic polymers and carbohydrates in solubilizing meconium, whose presence is responsible for various cases of pulmonary surfactant inactivation. In this regard, the invention provides a means for ravaging the uterus by infusion with an aqueous solution of the nonionic hydrophilic polymer or carbohydrate, with or without surfactant. The invention is thus useful in reducing abnormally high meconium concentrations in the amniotic fluid or correcting conditions arising from an abnormal reduction in the volume of amniotic fluid.

The usefulness of the nonionic hydrophilic polymers and carbohydrates in removing thick airway secretions and in solubilizing meconium extends the utility of these compounds beyond that of enhancing the effectiveness of a surfactant and is independent of the presence or absence of surfactant. The invention thus finds utility in the treatment of a wide range of conditions, including those which respond to pulmonary surfactant treatment as well as those in which excessive or highly concentrated meconium or other pulmonary secretions poses a threat to the health and safety of fetuses, children and adults alike.

Other aspects, objects, features, and advantages of the invention will become apparent from the description that follows.

BRIEF DESCRIPTION OF THE FIGURE

The FIGURE accompanying this specification is a plot of deflation pressure vs. volume for rat lungs. The points forming the upper curve are data taken on normal rat lungs with no treatment; the points forming the lower curve are data on rat lungs that were instilled with a mixture of meconium and pulmonary surfactant; and the points forming the middle curve are data on rat lungs that were instilled with a mixture of meconium, pulmonary surfactant, and an additive in accordance with the present invention.

DETAILED DESCRIPTION OF THE INVENTION AND PREFERRED EMBODIMENTS

Figure 1:
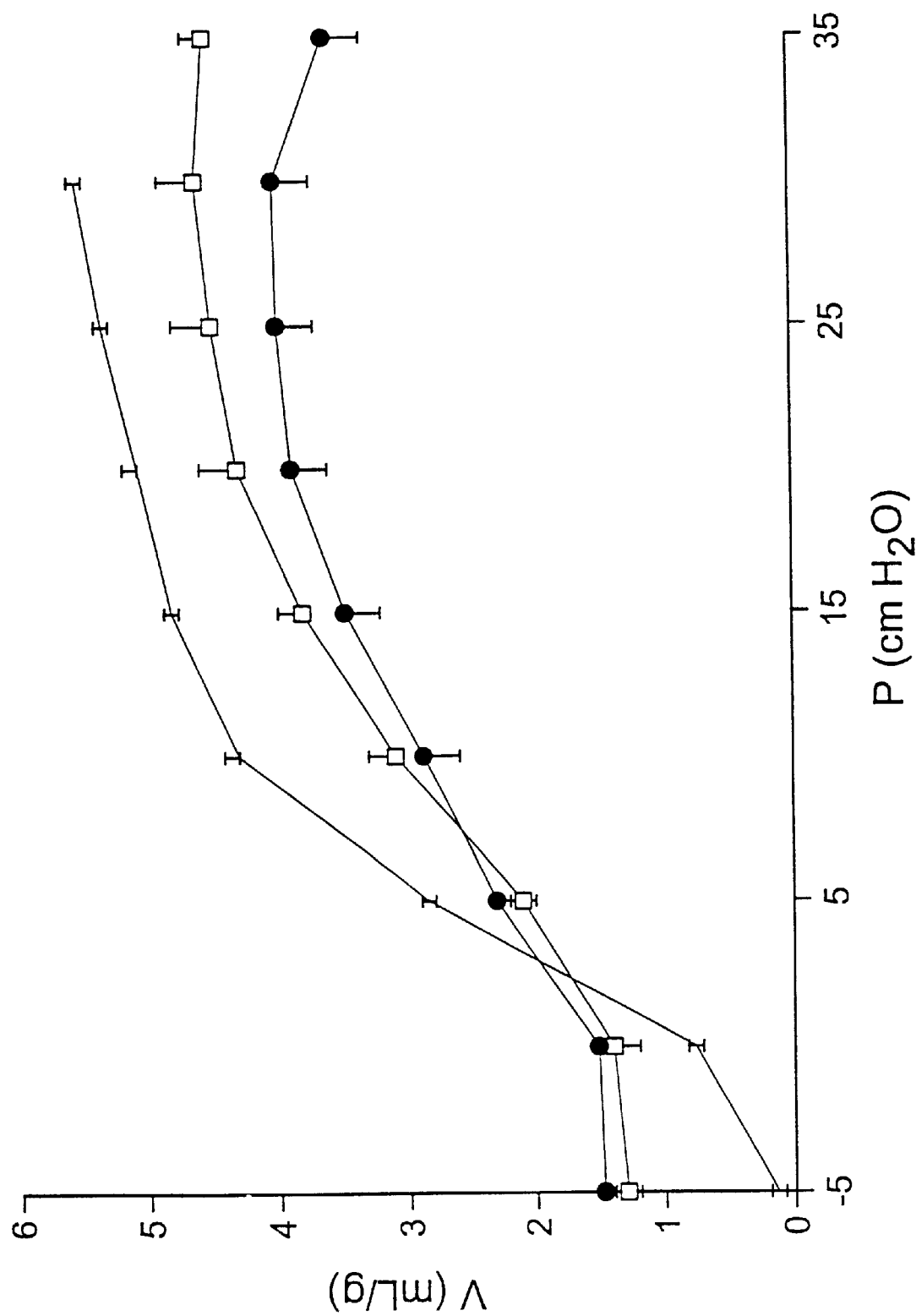

The additives utilized in the practice of this invention fall into two overlapping groups—nonionic hydrophilic polymers and carbohydrates. Each group is broad in scope but contains portions that are preferred either due to their effectiveness, consistency in performance, biocompatibility, economic factors, or other aspects of their performance or use.

The nonionic hydrophilic polymers are generally nonionic polymers that are pharmaceutically acceptable for administration to animals or humans. Useful polymers include those that are naturally occurring or derived from natural (plant or animal) sources as well as those that are or can be synthesized in the laboratory by polymerization of monomers. Examples of the various classes of nonionic hydrophilic polymers suitable for use in this invention are polysaccharides, poly(alkylene glycols), and polyamides. Other classes will be readily apparent to those skilled in the art. Examples of polysaccharides are celluloses, hemicelluloses, derivatives of cellulose and hemicellulose (such as esters, acetates, nitrates, and ethers of celluloses and hemicelluloses, as well as alkylcelluloses), lignin, dextran, dextrins, starches, and water-soluble gums (such as algins, carageenans, guar and locust bean gums, gum arabic, pectins, and xanthan). Preferred polysaccharides are dextran, starches, and water-soluble gums, with dextran and starches more preferred, and dextran particularly preferred. A preferred poly(alkylene glycol) is poly(ethylene glycol) (PEG). A preferred polyamide is poly(vinyl pyrrolidone) (PVP).

The molecular weight of the nonionic hydrophilic polymers can vary widely. The choice of an optimum molecular weight for any particular polymer will depend on how the molecular weight affects the solubility of the polymer and its biocompatibility, i.e., the ease and safety with which it can be administered through the trachea of a patient. In addition, however, varying the molecular weights of certain polymers can affect the degree to which these polymers can protect the surfactant from inactivation. In general, the most effective polymers are those with molecular weights that exceed about 500 daltons, preferably those that exceed about 1,000 daltons, and most preferably those that exceed about 3,000 daltons.

The proportion of the polymer relative to the surfactant can also vary. Higher proportions of polymer will generally have a greater effect in preventing or eliminating inactivation. In general, best results are achieved with polymer:surfactant proportions in the range of about 0.5:1 to about 10:1, preferably about 1:1 to about 5:1, and most preferably about 1.5:1 to about 3:1 all on a weight basis.

The carbohydrates group includes monosaccharides, oligosaccharides (including disaccharides), and polysaccharides. This group thus includes the polysaccharides listed above, as well as other saccharides of lesser chain length and the monomeric sugars themselves. The monosaccharides include pentoses, hexoses and heptoses, linear and cyclic, in both pyranose and furanose rings. Prominent carbohydrates in this group are monosaccharides and disaccharides. Specific examples are sucrose, glucose, mannose, maltose, arabinose, and galactose. Mannose is particularly preferred. The proportion of carbohydrate relative to the surfactant will vary as in the case of the polymer additives described above, with the same preferred proportion ranges.

The surfactants used in the practice of this invention are those that are effective in the treatment of pulmonary disorders, abating symptoms of these disorders. The surfactants include biological substances that are obtained directly from animal sources, substances that are derived from those obtained from animal sources and then treated by supplementation, extraction, or purification, and synthetic substances that are formulated to perform in the same or a similar manner as those that are naturally derived.

For surfactants that are animal-derived, either directly or with subsequent treatment, preferred sources are mammalian lungs. Examples of these sources are bovine lung, ovine lung, porcine lung, and dog lung. A variety of animal-derived surfactants are commercially available. Examples are as follows. In these examples, the terms "SP-A," "SP-B," "SP-C," and "SP-D" refer to four specific surfactant proteins that have been isolated from naturally-occurring pulmonary surfactants and identified by researchers. The proteins are widely cited by these names in the published literature on pulmonary surfactants.

SURFACTANT TA (available from Surfacten, Tokyo Tanabe, Tokyo Japan): prepared from organic solvent extractions of minced bovine lung. The surfactant contains 1% SP-B, 1% SP-C, 8% palmitic acid, 7% tripalmitin, and 84% phospholipids, supplied as a lyophilized powder for reconstitution with saline.

SURVANTA (available from Beractant, Abbott Laboratories, North Chicago, Ill., USA): a natural bovine extractant containing phospholipids, neutral lipids, fatty acids, and surfactant-associated proteins to which dipalmitoyl phosphatidylcholine (DPPC), palmitic acid, and tripalmitin are added, supplied as a liquid. The composition of this surfactant is 25 mg/mL phospholipids (including 11.0–15.5 mg/mL DPPC), 0.5–1.75 mg/mL triglycerides, 1.4–3.5 mg/mL free fatty acids, no cholesterol, and less than 1 mg/mL SP-B and SP-C.

Calf Lung Surfactant Extract (available from CLSE, Rochester, N.Y., USA):

prepared from calf lung lavage from which lipids and hydrophilic proteins are extracted. The product contains 63% saturated phosphatidylcholine, 32% other phospholipids, 4% cholesterol and cholesterol esters, and 1% hydrophobic protein (SP-B and SP-C).

INFASURF (available from Forrest Laboratories, St. Louis, Mo., USA): a chloroform-methanol extract of neonatal calf lung lavage without supplements. The product contains 35 mg/mL phospholipids, 55–70% of which is saturated phosphatidylcholine, plus SP-B and SP-C but no SP-A.

ALVEOFACT (available from Thomae GmbH, Biberach, Germany): obtained from bovine lung lavage and contains 1% SP-B and SP-C, 88% phospholipids, 4% cholesterol, and other lipids as the remainder.

CUROSURF (available from Chiesi Farmaceutici, Parma, Italy): prepared from minced pig lung by chloroform-methanol extraction and liquid-gel chromatography. The product contains 41–48% saturated phosphatidylcholine, 51–58% other phospholipids, and about 1% SP-B and SP-C, with no triglycerides, cholesterol or free fatty acids.

bLES (available from Biochemicals, Inc., London, Ontario, Canada): bovine lipid extract surfactant obtained by bovine lung lavage. This surfactant contains all of the phospholipids of natural surfactant plus SP-B and SP-C, but SP-A has been removed. The composition of the product is 79.2% phosphatidylcholine, 14.4% phosphatidylglycerol, 3% phosphatidylethanolamine, 2% sphingomyelin, 2% lysophosphatidylcholine, and trace amounts of lyso-bis-phosphatidic acid.

Examples of synthetic pulmonary surfactants are:

EXOSURF (available from Burroughs Wellcome, Research Triangle Park, N.C., USA). This is a protein-free surfactant containing 85% DPPC, 9% cetyl alcohol, and 6% tyloxapol (an ethoxylated-tert-octylphenol-polymethylene polymer).

Artificial Lung Expanding Compound (ALEC) (available from Pumactant, Britannia Pharmaceuticals, Redhill, Surrey, England). This is a protein-free surfactant containing DPPC and unsaturated phosphatidylglycerol in a weight ratio of 7:3.

PLM-C/B: containing DPPC, phosphatidylglycerol, and palmitic acid in a weight ratio of 68.5:22.5:9 plus 2% human recombinant SP-C and 1% natural bovine SP-B.

$KL_4$ (reported by Cochrane, C. G., et al., in "Pulmonary surfactant protein B (SP-B): structure-function relationships," Science 254:566–568 (1991), and "Protein-phospholipid interactions in pulmonary surfactant," Chest 105 (Suppl 3):37S–62S (1994)): a 21-residue polypeptide made from repeated sequences of one lysine and four leucine residues, simulating the hydrophobic and hydrophilic domains of the native SP-B molecule.

All percentages and ratios in this specification are on a weight basis, unless otherwise specified.

In the practice of this invention, the additive(s) are administered either before, during or after the administration of the surfactant(s), and in any case, both are administered directly to the lung of the patient or other region where therapy is needed. In a particularly convenient method, the additive(s) and surfactant(s) are combined in a single aqueous liquid formulation which is then administered to the patient. Suitable methods of administration are the same as those presently considered suitable and effective for surfactant therapy in general. The most direct and effective method is instillation of the composition into the lung through the trachea. Both surfactant and additive are generally administered as a liquid solution in buffered physiological saline. The amounts of both that are administered will be based on a surfactant dosage in accordance with the dosages currently used for surfactant therapy. Typical surfactant dosages are in the range of from about 30 to about 300 milligrams of surfactant per kilogram of patient body weight, and preferably from about 75 to about 125 mg/kg. The amount of additive administered is in accordance with the proportions indicated above.

The additives listed above are useful in the practice of this invention to supplement and improve surfactant therapy for a variety of disorders, abnormal conditions, and diseases. Examples are hyaline membrane disease, neonatal respiratory distress syndrome, acute respiratory distress syndrome, acute lung injury (such as that resulting from ozone inhalation, smoke inhalation, or near drowning), conditions of surfactant inactivation such as volutrauma and barotrauma, conditions of thick respiratory secretions (such as those arising from alveolar proteinosis, asthma, cystic fibrosis, or bronchiectasis), meconium aspiration syndrome, capillary leak syndrome, and bacterial or viral pneumonia.

In the use of this invention for the treatment or abatement of meconium-related conditions, the additive(s) are useful even in the absence of surfactant. In this regard, the nonionic hydrophilic polymers or carbohydrates are used for amnio-infusion to correct conditions that are indicated by meconium-stained amniotic fluid or by either an excess of meconium or a deficit in amniotic fluid volume in general. This aspect of the invention is particularly useful in pregnancies after rupture of the membrane. A saline solution of the hydrophilic polymer or carbohydrate is used for lavage of the fetus in utero.

The following examples are offered for purposes of illustration only, and are not intended to impose limits on the scope of the invention.

EXAMPLES

General Procedures

The meconium used in these experiments was first-pass meconium from term infants. In pilot experiments, little difference was found between the effects observed when using fresh meconium, frozen meconium or lyophilized meconium. Fresh meconium was used for in vitro experiments and lyophilized meconium was used for in vivo experiments.

Surfactants were diluted from 25 mg/mL solutions, using 5 mM HEPES (N-2-hydroxyethylpiperazine-N'-2-ethanesulfonic acid) buffer with 0.9% NaCl, pH 7–7.2, as a diluent. For experiments using meconium, the meconium was added to the surfactant preparation, which either already contained the additive or to which the additive was later added, and the resulting mixture was mixed at room temperature until the mixture was uniformly coffee beige in color. These mixtures usually contained particulates less than 1 mm in diameter. These particulates were removed by drawing and expelling the mixtures through a 25-gauge needle.

The Survanta used in these experiments was obtained from Ross/Abbott Laboratories, Columbus, Ohio, USA. Survanta that did not lower the surface tension below 10 mN/m was discarded and not used. Biochemicals were obtained from Sigma Chemical Company, St. Louis, Mo., USA. The water used in these experiments was rendered ultrapure by filtration, reverse osmosis, and dionization (18 MΩ-cm).

Surface tension measurements were taken on a pulsating bubble surfactometer (supplied by Electronetics, Amherst, N.Y., USA) as modified by Putz, G., et al., "Comparison of captive and modified pulsating bubble surfactometers," Journal of Applied Physiology 76:1425–31 (1994). To obtain the measurements, a sample was placed in a new 25-$\mu$L chamber, a 0.27-$\mu$L bubble was drawn into the sample, and the surface tension was measured over 10 seconds. Then, while the sample chamber temperature was maintained at 37° C., the bubble was cycled at a rate of 20 cycles per minute between volumes of 0.27 $\mu$L and 0.70 $\mu$L while the pressure was measured. Surface tension was estimated by the Laplace formula (P=2ST/r). The device was calibrated by a water manometer and by the use of pure fluids with known surface tension. The minimum surface tension after the tenth bubble deflation was used as the basis for comparison between the samples.

Viscosities were measured in either of two ways: (a) by recording the time for microliter amounts of the test fluid to run down a clean 20-cm PLEXIGLAS® plate held at a 45° angle, or (b) by timing the rate of egress of 0.5 mL of the test fluid from a vertical 1-mL plastic syringe through a 19-gauge needle at room temperature. Survanta in concentrations of 12.5 mg/mL in HEPES saline buffer was used with or without 5% meconium, and dextran (8,500 daltons) or polyethylene glycol (10,000 daltons) was added in concentrations of 5% by weight for viscosity experiments.

White Sprague Dawley rats of either sex weighing 250–300 g were used in the experiments. The animals were sacrificed by intraperitoneal injections of pentobarbital. A tracheostomy was performed using a 14-gauge catheter. The abdomen was incised. The diaphragm was opened bilaterally. The lungs were degassed by placing the rat with a patent airway in a Bell jar and lowering barometric pressure almost to water vapor pressure. Air inflation and deflation were achieved by use of a 30-mL syringe attached to the tracheal cannula, and pressure changes were measured at the trachea with a GM3 pressure transducer and WindowGraf chart recorder (Gould Electronics, Oxnard, Calif., USA). Total lung capacity was defined as the volume of air in the lungs at an inflating pressure of 30–35 cm $H_2O$ after a period of stabilization (about 45 seconds or when <0.1 mL of air entered in ten seconds). Deflation pressure vs. volume measurements were made by withdrawing air from the syringe to reduce pressure in 5-cm $H_2O$ decrements, allowing 20 seconds for pressure to stabilize at each step. Volumes were corrected for compression of gas in the apparatus. Control pressure-volume curves were obtained for all animals. Repeat degassing was performed if the lungs did not appear airless at the end of the control pressure volume maneuver. A mixture of Survanta (25 mg/mL) with 5% lyophilized meconium, with or without 5% polyethylene glycol (10,000 daltons) was then instilled. The lungs were inflated five times to distribute the mixture, and the pressure-volume curve was repeated. Lung volume results were recorded as mL/g of estimated lung weight. Lungs from 8 normal rats were weighed, yielding a lung weight of 0.8±0.4% (mean± S.E.M.) Pressure-volume relationships were analyzed using analysis of variance for repeated measurements.

Example 1

This example illustrates the effectiveness of various additives within the scope of this invention in lessening the ability of meconium to inactivate the surface tension-lowering activity of Survanta. Using the pulsating bubble surfactometer and procedure described above, measurements were taken on test samples that consisted of Survanta (at 1.25 mg/mL), various amounts of meconium (ranging from none to 3% on a weight/volume basis, i.e., 0 to 30 mg/mL of the sample), and various additives (dextran (282,000–500,000 daltons), polyethylene glycol (8,000–10,000 daltons), poly(vinyl pyrrolidone) (10,000–40,000 daltons), agarose, and SP-A). In each case, the meconium was added after the additive and surfactant were combined. The mean values and S.E.M. (standard error of the mean) values were taken for a minimum of four replicates of each sample. The results are listed in Table I, where measurements taken with dog surfactant are included for comparison.

TABLE I

Surface Tension Measurements With Various Additives in Presence of Meconium

| Surfactant | Additive | Minimum Surface Tension (mN/m) ± S.E.M. | | | |
|---|---|---|---|---|---|
| | | 0% meconium | 1% meconium | 2% meconium | 3% meconium |
| Survanta, 1.25 mg/mL | (none) | 3 ± 0.3 | 22 ± 1.4 | 27 ± 2.2 | 30 ± 2.9 |
| Survanta, 1.25 mg/mL | Dextran 282–500 kD, 5%–10% | 0 ± 0.1 | 1 ± 0.3 | 2 ± 0.6 | 2 ± 0.6 |
| Survanta, 1.25 mg/mL | PEG 8–10 kD, 5%–10% | 0 ± 0.1 | 1 ± 0.3 | 1 ± 0.3 | 1 ± 0.5 |
| Survanta, 1.25 mg/mL | PVP 10–40 kD, 5%–10% | 1.5 ± 0.7 | 2 ± 0.7 | 2.5 ± 1.0 | 2 ± 2.6 |
| Survanta, 1.25 mg/mL | Agarose, 0.1% (n = 2) | 6 | 10 | 8 | 26 |
| Survanta, 1.25 mg/mL | SP-A, 3% | 6 ± 0.6 | 6 ± 1.0 | 17 ± 1.4 | 25 ± 3.5 |
| Dog Surfactant, | (none) | 4 ± 1.8 | 6 ± 2.5 | 7 ± 2.0 | 5 ± 2.5 |

TABLE I-continued

Surface Tension Measurements With Various Additives in Presence of Meconium

| Surfactant | Additive | Minimum Surface Tension (mN/m) ± S.E.M. | | | |
|---|---|---|---|---|---|
| | | 0% meconium | 1% meconium | 2% meconium | 3% meconium |
| 1.25 mg/mL (none) | (none) | 68 ± 0.1 | 52 ± 2.0 | 48 ± 1.5 | 46 ± 4.0 |
| (none) | PEG 10 kD, 5% | 51 ± 1.5 | 46 ± 2.0 | 44 ± 1.5 | 47 ± 3.5 |
| (none) | Dextran 9.5 kD | 50 ± 0.5 | 47 ± 1.5 | 47 ± 2.0 | 47 ± 2.5 |

This data shows that dextran, PEG, and PVP, when added to Survanta, each prevent an increase in surface tension (and in fact do so to a greater extent than SP-A) after meconium has been added to the mixture, and therefore prevent inactivation of the surfactant by the meconium. Agarose also lessens the inactivation, although to a lesser degree. The last three rows in the table show that neither meconium, dextran, nor PEG by themselves lower the surface tension to less than 40 mN/m.

Example 2

This example illustrates the effectiveness of two of the additives of this invention (PEG and PVP) in enhancing the surface tension-lowering effect of Survanta even when no meconium is present. Four dilutions of the surfactant were used, and each data entry is a mean± S.E.M. for three replicates. Otherwise the procedure was the same as that of Example 1. The results are listed in Table II below.

TABLE II

Effect of Additives in Enhancing Activity of Surfactant in Absence of Meconium

| | Minimum Surface Tension (mN/m) ± S.E.M. | | |
|---|---|---|---|
| Surfactant | No additive | 5% Dextran 9.5 kD | 5% PEG 10 kD |
| Survanta, 1.25 mg/mL | 6 ± 1.8 | 0 ± 0.1 | 1 ± 1.2 |
| Survanta, 0.62 mg/mL | 17 ± 2.9 | 0 ± 0.1 | 0 ± 0.1 |
| Survanta, 0.31 mg/mL | 29 ± 7.6 | 4 ± 2.3 | 1 ± 0.6 |
| Survanta, 0.16 mg/mL | 47 ± 4.1 | 21 ± 4.7 | 22 ± 4.7 |

This data shows that at all dilutions tested, the additives enhance the ability of the surfactant to lower surface tension even with no meconium present.

Example 3

This example illustrates the effectiveness of various different molecular weights of three polymeric additives within the scope of this invention in lessening the ability of meconium to inactivate the surface tension-lowering ability of Survanta. The additives tested were dextran, PEG and PVP, and the molecular weights ranged from 200 daltons to 500,000 daltons. Four or more replicates were averaged for each data entry. The procedures were otherwise the same as those of Example 1. The results are listed in Table III.

TABLE III

Effect of Additive Molecular Weight on Surfactant Activity in Presence of 3% Meconium

| | Mininium Surface Tension (mN/m) ± S.E.M. | | |
|---|---|---|---|
| Additive Molecular Weight | Dextran (5–10%) | PEG (5–10%) | PVP (5–10%) |
| 200 D | | 29 ± 0.7 | |
| 3.3–10 kD | | 2 ± 0.3 | |
| 10 kD | | | 11 ± 3.5 |
| 40 kD | | | 1 ± 1.0 |
| 9.5–68.4 kD | 1 ± 0.3 | | |
| 148 kD | 1 ± 0.4 | | |
| 282–500 kD | 2 ± 0.6 | | |

The data show that all molecular weights in excess of 3.3 kD were effective in reducing meconium inactivation of the surfactant.

Example 4

This example illustrates the effect of varying the additive concentration for three of the polymeric additives of this invention on their ability to lessen the tendency of meconium to inactivate Survanta. The additives tested were dextran, PEG and PVP, at concentrations of 1%, 5% and 10%, all by weight, with four or more replicates averaged for each data entry. The procedures were otherwise the same as those of Example 1. The results are listed in Table IV.

TABLE IV

Effect of Additive Concentration on Surfactant Activity in Presence of 3% Meconium

| | Minimum Surface Tension (mN/m) ± S.E.M. | | |
|---|---|---|---|
| Additive | 1% | 5% | 10% |
| Dextran 9.5 kD | 10 ± 8 | 1 ± 2 | 0 ± 0 |
| PEG 8–10 kD | 5 ± 6 | 1 ± 2 | 1 ± 1.5 |
| PVP 10–40 kD | 26 ± 7 | 7 ± 7 | 2 ± 2 |

The data shows that best results with these three polymeric additives are obtained when using concentrations greater than 1% by weight.

Example 5

This example illustrates the effectiveness of the additives of this invention when added after the surfactant and meconium had been combined, as opposed to combining the surfactant and additive first and then adding the meconium as in the preceding examples. This example thus demonstrates the ability of the additives to reverse the inactivating effect of the meconium after the inactivation has occurred. In some of the tests, serum proteins and lysophosphatidylcholine were used in place of meconium as the surfactant inactivating agent. The additives tested were dextran and PEG, each at concentrations of 5–10% by weight, and each at molecular weights of 3.3 kD to 500 kD. The procedures were otherwise the same as those of Example 1. The results are listed in Table V, where each data entry is the average of at least four replicates and all percents shown are weight/volume.

TABLE V

Effect of Additives in Reversing Surfactant Inactivation Caused by Meconium and Other Inactivators

| | | Minimum Surface Tension (mN/m) ± S.E.M. | | |
|---|---|---|---|---|
| Surfactant | Inactivator | No Additive | Dextran | PEG |
| Survanta, 1.25 mg/mL | 1% Meconium | 25 ± 3.6 | 4 ± 2.8 | 1 ± 0.7 |
| Survanta, 1.25 mg/mL | 2% Meconium | 27 ± 6 | 8 ± 4 | 0 ± 0.3 |
| Survanta, 1.25 mg/mL | 3% Meconium | 30 ± 6 | 8 ± 3.2 | 1 ± 0.4 |
| Survanta, 1.25 mg/mL | 10% Lyso-phosphatidyl-choline | 23 ± 1.8 | 1 ± 0.1 | 0 ± 0.1 |
| Survanta, 1.25 mg/mL | 1% Serum Proteins | 22 ± 1.8 | 1 ± 0.1 | 0 ± 0.1 |

The data shows that both polymers effectively reverse the inactivation of Survanta that has already occurred as a result of contact with meconium, lysophosphatidylcholine, and serum proteins.

Example 6

This example illustrates the effectiveness of simple sugars as additives for lessening the ability of meconium to inactivate Survanta. The sugars tested were glucose, mannose, maltose, and galactose. In individual tests, these sugars were added separately to Survanta before the addition of 0.1–3% meconium. The best results were obtained with mannose at 10% concentration. The Survanta-mannose mixtures lowered surface tension to less than 12 mN/m in 69% of the trials in the presence of 0.2% of lyophilized meconium.

Example 7

This example demonstrates the ability of the additives of this invention in lowering the viscosity of solutions of surfactant, both in the presence of and in the absence of meconium. The syringe method described above was used to measure the viscosities, and measurements were taken on solutions of Survanta alone, Survanta with each of the additives PEG and dextran, the additives alone, and the HEPES saline solution containing neither Survanta nor the additives. Measurements in each case were taken both in the presence and the absence of 5% meconium. The results are listed in Table VI.

TABLE VI

Viscosity Measurements -- Effects of Surfactant, Meconium, and Additives

| | Viscosity (sec) ± S.E.M. | |
|---|---|---|
| Species in Test Mixture | No Meconium | 5% Meconium |
| Survanta | 39 ± 15 | 40 ± 9 |
| Survanta + 5% PEG | 6 ± 0.5 | 16 ± 3 |
| Survanta + 5% Dextran | 7 ± 3 | 18 ± 3 |
| (Saline only) | 3 ± 0 | 6 ± 1 |
| Saline + 5% PEG | 6 ± 1 | 8 ± 1 |
| Saline + 5% Dextran | 4 ± 1 | 9 ± 1 |

These data indicate that the polymeric additives used in this example lower the viscosity of Survanta solutions both in the presence of and the absence of meconium.

Example 8

This example presents in vivo test results on rats and reports deflation pressure vs. lung volume and how this relation is affected by the injection of a surfactant-meconium mixture and by the injection of a surfactant-meconium-additive mixture.

The procedures described above were used. Twelve animals were used in each experimental group for determination of total lung capacity, and nine animals were used for each experimental group for measurement of pressure-volume relationships. In one experimental group, the test mixture contained 25 mg/mL Survanta and 5% meconium. In the other, the test mixture contained 25 mg/mL Survanta, 5% meconium, and 5% PEG (10 kD). The amount of each test mixture administered in each case was that which provided 4 mg/kg of body weight.

The total lung capacity measurements revealed that in the untreated lungs, filling of the lungs occurred at 30 cm $H_2O$ pressure, whereas in the lungs treated with either of the two test mixtures, filling of the lungs required 35 cm $H_2O$.

The deflation pressure-volume relationship measurements are shown in the attached FIGURE, where the volume is expressed in milliliters per gram of estimated lung weight, and the pressure is expressed in centimeters of water. The upper curve of the FIGURE represents the pretreatment (control) measurements, which gave the same results for the two groups of animals and are therefore combined into a single curve. The lower curve (using filled diamonds as data points) represents the measurements taken on lungs injected with the test mixture containing Survanta and meconium only, and the middle curve (using open squares as data points) represents the measurements taken on lungs injected with the test mixture containing Survanta, meconium, and PEG.

Both the control curve and the curve representing the Survanta-meconium-PEG treated group are significantly higher than the curve representing the group treated with Survanta and meconium only. Comparing values from the lower and middle curves with those of the upper curve, the total lung capacity for the animals treated with Survanta and meconium only is reduced to 70±3% of the control, while the total lung capacity for the animals treated with Survanta-meconium-PEG is reduced only to 88±3% of the control. The difference is significant (Student t test: $p<0.05$).

The foregoing is offered primarily for purposes of illustration. It will be readily apparent to those skilled in the art that the materials and methods of administration may be further modified or substituted in various ways without departing from the spirit and scope of the invention.

What is claimed is:

1. A composition comprising an aqueous liquid solution of:
   (a) surfactant effective in the abatement of symptoms of pulmonary disorders, and
   (b) a nonionic hydrophilic polymer selected from the group consisting of polysaccharides, poly(alkylene glycol), and polyamides, in which said nonionic hydrophilic polymer and said surfactant are at a weight ratio of from about 0.5:1 to about 10:1.

2. A composition in accordance with claim 1 in which said surfactant is animal-derived surfactant.

3. A composition in accordance with claim 1 in which said surfactant is a naturally-occurring substance extracted from mammalian lung.

4. A composition in accordance with claim 1 in which said surfactant is a naturally-occurring substance extracted from a member selected from the group consisting of bovine lung, porcine lung, ovine lung, and dog lung.

5. A composition in accordance with claim 1 in which said surfactant is a mixture of (i) a naturally-occurring substance extracted from a member selected from the group consisting of bovine lung, porcine lung, and ovine lung, and (ii) a pharmaceutically acceptable substance that increases the surface tension-lowering activity of said naturally-occurring substance.

6. A composition in accordance with claim 1 in which said surfactant is surfactant extracted from bovine lung supplemented with dipalmitoyl phosphatidylcholine, palmitic acid, and tripalmitin.

7. A composition in accordance with claim 1 in which said surfactant is a synthetic, protein-free surfactant comprised of a member selected from the group consisting of phosphatidyl choline, dipalmitoyl phosphatidylcholine, phosphatidylglycerol, phosphatidylinositol, phosphatidylethanolamine, phosphatidylserine, sphingomyelin, and lysophosphatidylcholine.

8. A composition in accordance with claim 1 in which said surfactant is a synthetic, protein-free surfactant comprised of a member selected from the group consisting of phosphatidyl choline, dipalmitoyl phosphatidylcholine, and phosphatidylglycerol.

9. A composition in accordance with claim 1 in which said surfactant is a synthetic, protein-free surfactant comprised of at least 75% by weight dipalmitoyl phosphatidylcholine.

10. A composition in accordance with claim 1 in which said nonionic hydrophilic polymer is a member selected from the group consisting of dextran, starches, poly(ethylene glycol), and poly(vinyl pyrrolidone).

11. A composition in accordance with claim 1 in which said nonionic hydrophilic polymer is a member selected from the group consisting of dextran, poly(ethylene glycol), and poly(vinyl pyrrolidone).

12. A composition in accordance with claim 1 in which said nonionic hydrophilic polymer is dextran.

13. A composition in accordance with claim 1 in which said nonionic hydrophilic polymer is poly(ethylene glycol).

14. A composition in accordance with claim 1 in which said nonionic hydrophilic polymer and said surfactant are at a weight ratio of from about 1:1 to about 5:1.

15. A composition in accordance with claim 1 in which said nonionic hydrophilic polymer and said surfactant are at a weight ratio of from about 1.5:1 to about 3:1.

16. A method for the treatment of a patient suffering from respiratory distress syndrome, said method comprising administering to said patient a therapeutically effective amount of a composition comprising an aqueous liquid solution of:
   (a) a surfactant effective in the abatement of symptoms of pulmonary disorders, and
   (b) a nonionic hydrophilic polymer selected from the group consisting of polysaccharides, poly(alkylene glycol), and polyamides, in which said nonionic hydrophilic polymer and said surfactant are at a weight ratio of from about 0.5:1 to about 10:1, and said nonionic hydrophilic polymer is in a proportion effective in substantially inhibiting endogenous substances in said patient from inactivating said surfactant.

17. A method in accordance with claim 16 in which said surfactant is animal-derived surfactant.

18. A method in accordance with claim 16 said surfactant is a naturally-occurring substance extracted from mammalian lung.

19. A method in accordance with claim 16 in which said surfactant is a naturally-occurring substance extracted from a member selected from the group consisting of bovine lung, porcine lung, ovine lung, and dog lung.

20. A method in accordance with claim 16 in which said surfactant is a mixture of (i) a naturally-occurring substance extracted from a member selected from the group consisting of bovine lung, porcine lung, and ovine lung, and (ii) a pharmaceutically acceptable substance that increases the surface tension-lowering activity of said naturally-occurring substance.

21. A method in accordance with claim 16 in which said surfactant is surfactant extracted from bovine lung supplemented with dipalmitoyl phosphatidylcholine, palmitic acid, and tripalmitin.

22. A method in accordance with claim 16 in which said surfactant is a synthetic, protein-free surfactant comprised of a member selected from the group consisting of phosphatidyl choline, dipalmitoyl phosphatidylcholine, phosphatidylglycerol, phosphatidylinositol, phosphatidylethanolamine, phoisphatidylserine, sphingomyelin, and lysophosphatidylcholine.

23. A method in accordance with claim 16 in which said surfactant is a synthetic, protein-free surfactant comprised of a member selected from the group consisting of phosphatidyl choline, dipalmitoyl phosphatidylcholine, and phosphatidylglycerol.

24. A method in accordance with claim 16 in which said surfactant is a synthetic, protein-free surfactant comprised of at least 75% by weight dipalmitoyl phosphatidylcholine.

25. A method in accordance with claim 16 in which said nonionic hydrophilic polymer is a member selected from the group consisting of dextran, starches, poly(ethylene glycol), and poly(vinyl pyrrolidone).

26. A method in accordance with claim 16 in which said nonionic hydrophilic polymer is a member selected from the group consisting of dextran, poly(ethylene glycol), and poly(vinyl pyrrolidone).

27. A method in accordance with claim 16 in which said nonionic hydrophilic polymer is dextran.

28. A method in accordance with claim 16 in which said nonionic hydrophilic polymer is poly(ethylene glycol).

29. A method in accordance with claim 16 in which said nonionic hydrophilic polymer and said surfactant are at a weight ratio of from about 1:1 to about 5:1.

30. A method in accordance with claim 16 in which said nonionic hydrophilic polymer and said surfactant are at a weight ratio of from about 1.5:1 to about 3:1.

* * * * *